US010821046B2

(12) United States Patent
Hares et al.

(10) Patent No.: US 10,821,046 B2
(45) Date of Patent: Nov. 3, 2020

(54) ROBOT MOUNTING ARRANGEMENT

(71) Applicant: CMR SURGICAL LIMITED, Cambridge (GB)

(72) Inventors: Luke David Ronald Hares, Cambridge (GB); Keith Marshall, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

(21) Appl. No.: 16/060,580

(22) PCT Filed: Dec. 9, 2016

(86) PCT No.: PCT/GB2016/053905
§ 371 (c)(1),
(2) Date: Jun. 8, 2018

(87) PCT Pub. No.: WO2017/098278
PCT Pub. Date: Jun. 15, 2017

(65) Prior Publication Data
US 2019/0000706 A1    Jan. 3, 2019

(30) Foreign Application Priority Data

Dec. 10, 2015    (GB) .................................. 1521813.4

(51) Int. Cl.
*F16M 13/00* (2006.01)
*A61G 13/10* (2006.01)
(Continued)

(52) U.S. Cl.
CPC ............ *A61G 13/101* (2013.01); *A61B 34/70* (2016.02); *A61B 90/57* (2016.02); *B25J 5/007* (2013.01);
(Continued)

(58) Field of Classification Search
CPC .......... B25J 9/1689; B25J 9/042; G09B 23/28
See application file for complete search history.

(56) References Cited

U.S. PATENT DOCUMENTS 5,184,601 A * 2/1993 Putman .................... B25J 9/042
312/209
5,597,146 A    1/1997 Putman
(Continued)

FOREIGN PATENT DOCUMENTS

DE    102012110193 A1    4/2014
WO    2015175218 A1    11/2015

OTHER PUBLICATIONS

International Search Report and Written Opinion from corresponding PCT/GB2016/053905 dated Feb. 15, 2017.
United Kingdom Search Report from corresponding United Kingdom Application No. GB1521813.4 dated Apr. 21, 2017.
Chinese First Notification of Office Action from corresponding Chinese Application No. 201680072027.9 dated Jul. 31, 2020.

*Primary Examiner* — Amy J. Sterling
(74) *Attorney, Agent, or Firm* — Lando & Anastasi, LLP

(57) ABSTRACT

A surgical robotic system comprising: a surgical robot arm (7, 8, 9) having at least six degrees of freedom, the arm having a distal end for attachment to a surgical tool (5) and a proximal end; and a mounting structure (10, 11, 12) configured to mate to the proximal end of the arm for holding the proximal end of the arm spatially fixed, the mounting structure comprising an electrical connection for powering the surgical robot arm; wherein the system comprises a manually operable latching mechanism (6) whereby the arm can be attached to and released from the mounting structure.

15 Claims, 3 Drawing Sheets

(51) Int. Cl.

| | |
|---|---|
| *B25J 9/00* | (2006.01) |
| *A61B 34/00* | (2016.01) |
| *A61B 90/57* | (2016.01) |
| *B25J 5/00* | (2006.01) |
| *B25J 9/04* | (2006.01) |
| *A61B 17/00* | (2006.01) |
| *A61B 34/30* | (2016.01) |
| *A61B 90/50* | (2016.01) |
| *B25J 9/16* | (2006.01) |

(52) U.S. Cl.
CPC ........... *B25J 9/0009* (2013.01); *B25J 9/0018* (2013.01); *B25J 9/047* (2013.01); *A61B 34/30* (2016.02); *A61B 90/50* (2016.02); *A61B 2017/00477* (2013.01); *A61B 2090/571* (2016.02); *B25J 9/162* (2013.01)

(56) References Cited

U.S. PATENT DOCUMENTS

| | | | |
|---|---|---|---|
| 6,246,200 B1* | 6/2001 | Blumenkranz | B25J 9/1689 |
| | | | 128/DIG. 7 |
| 8,663,203 B2 | 3/2014 | Tovey et al. | |
| 9,666,101 B2* | 5/2017 | Kumar | G09B 23/28 |
| 2006/0149418 A1 | 7/2006 | Anvari | |
| 2008/0065112 A1 | 3/2008 | Tovey et al. | |
| 2010/0012798 A1 | 1/2010 | Blum et al. | |
| 2012/0124824 A1* | 5/2012 | Burbank | A61B 34/70 |
| | | | 29/700 |
| 2015/0204167 A1* | 7/2015 | Skeels | E21B 33/038 |
| | | | 166/344 |
| 2015/0306770 A1 | 10/2015 | Mittal et al. | |

\* cited by examiner

ROBOT MOUNTING ARRANGEMENT

CROSS-REFERENCE TO RELATED APPLICATIONS

This application is a U.S. National Phase Application under 35 U.S.C. § 371 of International Application No. PCT/GB2016/053905, filed Dec. 9, 2016, which claims priority to United Kingdom Application No. 1521813.4, filed Dec. 10, 2015, which is hereby incorporated by reference in its entirety for all purposes.

BACKGROUND

This invention relates to robotic systems, for example for performing surgical tasks.

Various designs of robotic systems have been proposed for performing or assisting in surgery. However, many robot designs suffer from problems that make them unsuitable for performing a wide range of surgical procedures.

Normally, a surgical robot has at least one robot arm with a surgical tool attached to the distal end of the robot arm. A base supports the robot and is itself attached to, for example, the operating theatre floor, or a trolley. The arm extends between the base and the tool.

A robot arm may have one or more degrees of freedom. A robot arm typically has a plurality of articulations, which are used to locate the surgical tool in a desired location relative to the patient. For example, the arm may comprise one or more joints. The joints and the tool may be capable of being articulated to enable the robot to perform a surgical procedure.

Some surgical robots are of considerable bulk and comprise multiple robot arms stemming from a single floor-standing base. These systems are bulky, making them difficult to move into place in an operating theatre. In some surgical environments, there is not sufficient space to be able to locate a single-based robot in a convenient location near a particular operating site. Also, the range of possible spatial relationships between the arms is limited by the fact that the arms stem from a single base. This restricts the range of surgical procedures that can be carried out by such systems.

One way to increase the range of procedures that can be performed is to arrange for each arm to have a separate base. The base could then be smaller and more mobile than for a multi-arm robot. The separate bases could be on wheels and could be pushed around an operating theatre to suit the needs of a specific procedure. An alternative approach would be to fix arms to the ceiling or walls of the operating theatre by a medium such as bolts or adhesive. This would allow the arms to approach the operating table from different directions, which may be better suited to certain procedures. However, with both of these approaches, the range of movement of the arms is still restricted, so that a surgical assistant cannot easily move or reconfigure the arms so that substantially any surgical procedure can be carried out.

It is desirable in a surgical robotic system that the arms are relatively small and lightweight. These characteristics provide a number of advantages: for example that the arm is easier for a technician to position before surgery takes place and that more arms can be fitted closely together around a surgical site. Flexibility of positioning of the robot arms has the advantage that the equipment can perform a greater range of procedures than some other robotic systems. For example, surgery to the head or face may require a different configuration of robot arms to an abdominal operation, so it is desirable to be able to alter the configuration of arms quickly and easily between procedures.

There is a need for a robotic system that can successfully perform a wider range of surgical procedures than existing systems, where robot arms can be easily and manually re-configured.

SUMMARY

According to an aspect of the invention, there is provided a robotic system comprising a robot arm having at least six degrees of freedom, the arm having a distal end for attachment to a tool and a proximal end; a mounting structure configured to mate to the proximal end of the arm for holding the proximal end of the arm spatially fixed; and the system comprising a manually operable latching mechanism whereby the arm can be attached to and released from the mounting structure.

The manually operable latching mechanism may be integral with the robot arm.

The manually operable latching mechanism may be integral with the mounting structure.

The mounting structure may comprise a socket. The socket may be configured for receiving the proximal end of the arm when the arm is mated to the mounting structure. The socket may be generally of frustoconical form.

The mounting structure may have side walls that abut the proximal end of the arm when the arm is engaged with the mounting structure.

The mounting structure may comprise one or more electrical connections for powering the robot arm. The robot arm may comprise a plurality of electrical connectors configured for contacting the electrical connections of the mounting structure when the arm is mated to the mounting structure.

The mounting structure may comprise a communication connection for conveying data signals to or from the robot arm. The communication connection may be a physical connection or a wireless data transmitter.

The mounting structure may be fast with an article of operating theatre furniture or with the structure of an operating theatre.

According to a second aspect of the invention, there is provided a suite of robotic equipment comprising a robot arm having at least six degrees of freedom, the arm having a distal end for attachment to a tool and a proximal end; a plurality of mounting structures, each mounting structure being configured to mate to the proximal end of the robot arm for holding the proximal end of the arm spatially fixed; and the system comprising a manually operable latching mechanism whereby the arm can be attached to and released from any of the plurality of mounting structures.

The manually operable latching mechanism may be integral with one or both of the robot arm and the mounting structures.

Each of the plurality of mounting structures may comprise a socket.

Each of the plurality of mounting structures may have side walls that abut the proximal end of the arm when the arm is engaged with the respective mounting structure.

Each of the plurality of mounting structures may comprise a socket, optionally of frustoconical form, for receiving the arm when the arm is engaged with the respective mounting structure.

Each of the plurality of mounting structures may provide an electrical connection for powering the robot arm.

Each of the plurality of mounting structures may provide a communication connection for conveying data signals to or from the robot arm.

Each of the plurality of mounting structures may be fast with an article of operating theatre furniture or with the structure of an operating theatre. One of the mounting structures may be attached to a ceiling of the operating theatre. One of the mounting structures may be attached to a mobile cart. One of the mounting structures may be attached to an operating table. One of the mounting structures may be attached to a wall of the operating theatre. One of the mounting structures may be attached to a floor of the operating theatre. One of the mounting structures may be attached to a pedestal.

The suite of robotic equipment may comprise at least one further robot arm having at least six degrees of freedom. Each further arm may have a distal end for attachment to a tool and a proximal end. The proximal end of the at least one further arm may be configured to mate to each of the plurality of mounting structures.

BRIEF DESCRIPTION OF FIGURES

The present invention will now be described by way of example with reference to the accompanying drawings. In the drawings:

FIG. 2 shows examples of mounting structures.

DETAILED DESCRIPTION

Figure 1:
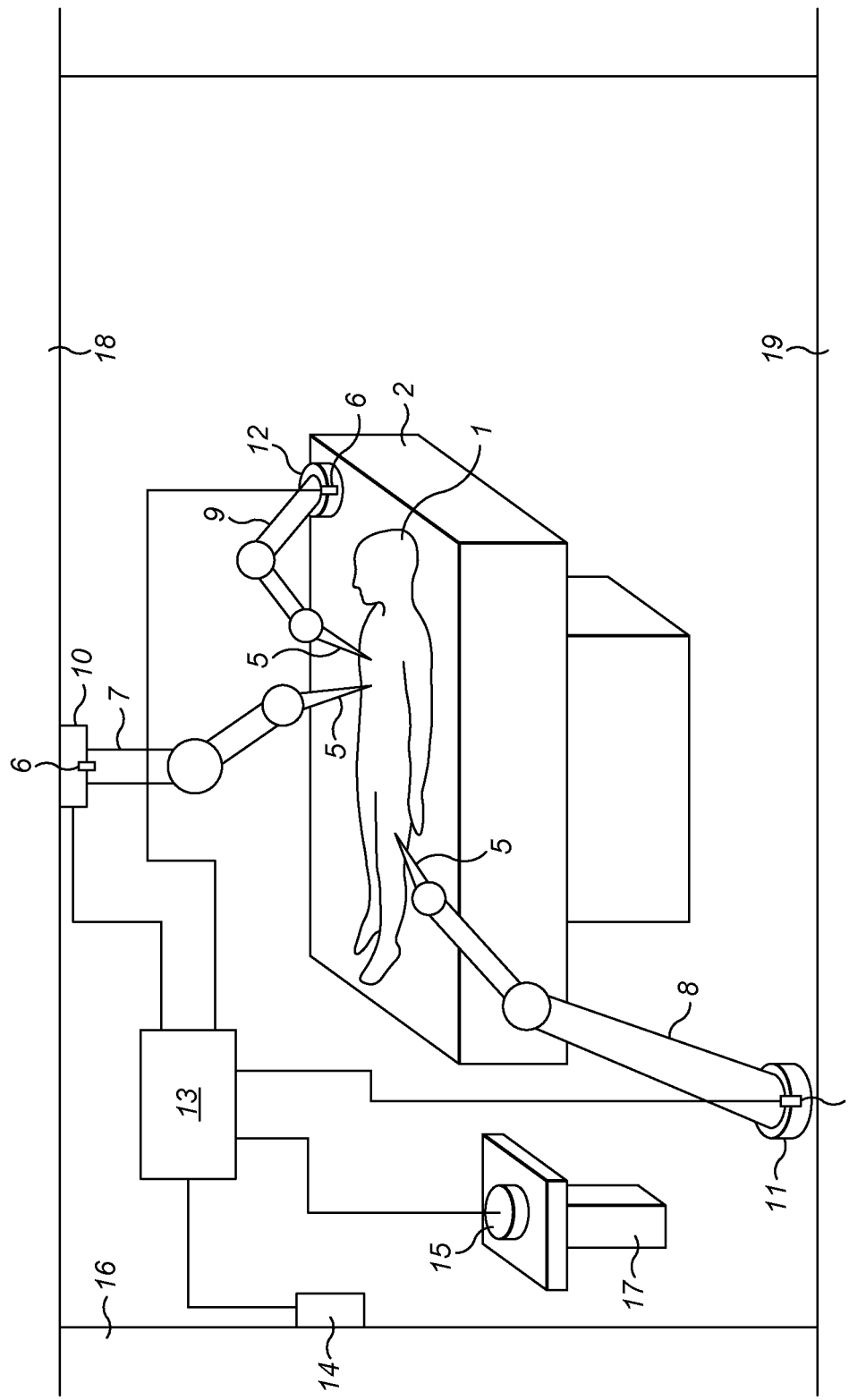
FIG. 1 shows a robotic system suitable for performing surgical procedures in an operating theatre.

FIG. 1 shows a robotic system suitable for performing surgical procedures in an operating theatre on a patient 1. The patient is on a bed or operating table 2. Three robot arms 7, 8 and 9 each have proximal ends configured to mate with one of three mounting structures 10, 11 and 12. Mounting structures 10, 11 and 12 are fixedly attached to the ceiling 18, floor 19 and bed 2 respectively of the operating theatre. Each arm is held in place in its respective mounting structure by a manually operable latching mechanism 6. The number of mounting structures within the operating theatre may be greater than the number of robot arms. The robot arms may be mated to alternative mounting structures 14 and 15, here fixedly attached the wall 16 of the operating theatre and to a pedestal 17 respectively. The configurations of each of the mounting structures match each other, and the configurations of the proximal ends of each of the robot arms match each other. As a result, any of the robot arms 7 to 9 may mate with any of the mounting structures 10 to 15 located at various positions around the operating theatre. This arrangement allows a theatre technician or surgical assistant to readily position the robot arms in a selected set of the mounting structures, located at positions relative to the patent that are most suitable for the specific procedure being performed.

Once the proximal end of a robot arm mates with a mounting structure of the type described herein, the proximal end of the arm can be held spatially fixed with respect to the mounting structure by way of a manually operable latching mechanism 6.

The robot arm extends from the mounting structure towards the patient. The distal end of the robot arm is suitable for attachment to a tool 5. The tool is designed for insertion into the patient and, for example, could be an endoscope or a cutting or pinching tool.

The robot arm may have at least six degrees of freedom. The motion of the arm may be provided by joints at various points along the arm. Each joint could permit rotational and/or linear relative motion of the arm portions on either side of it. The robot arm may thus be composed of a series of rigid elongate elements, each one being joined to the next via articulations which could permit rotation. The arm may be manoeuvrable at the proximal end, with at least one axis of rotation adjacent to the mounting structure.

Figure 2A:
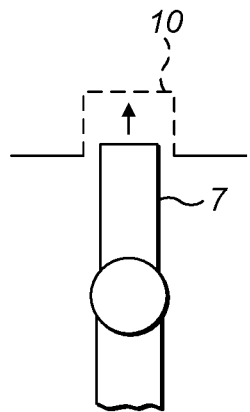
FIG. 2a shows a mounting structure comprising a socket.
Figure 2B:
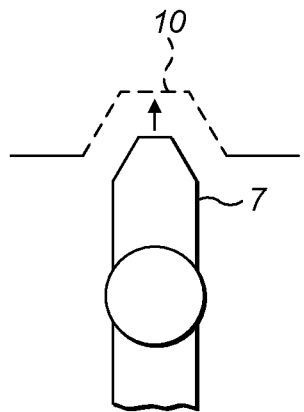
FIG. 2b shows a mounting structure comprising a frustoconical socket.
Figure 2C:
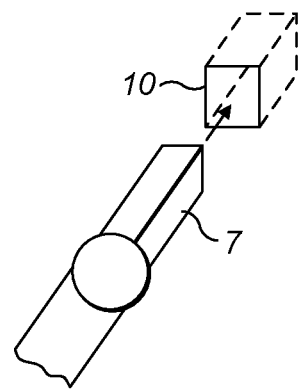
FIG. 2c shows a mounting structure having side walls which abut the proximal end of the robot arm when the arm is engaged with the mounting structure.

The mounting structure may comprise a socket, as shown in FIG. 2(a). The mounting structure and socket may be mutually configured to permit the two to mate firmly together with the arm held fast by the socket. This may be achieved by the mounting structure latching into the socket. The arm and the mounting structure may further be configured so that they can be manually separated, for example by releasing a latch holding the two together. The socket may be frustoconical in shape, as shown in FIG. 2(b). The mounting structure may have side walls that abut the proximal end of the arm when the arm is engaged with the mounting structure, as shown in FIG. 2(c).

When the arm is latched to the mounting structure there may be abutment in more than one axis between features of the arm and features of the mounting structure. This can result in the arm being fixed rigidly in place with respect to the mounting structure, once latched. It may further permit the arm to be self-locating in or on the mounting structure; this can make the installation of the arm with respect to the mounting structure easier. The mounting structure and the arm may be mutually configured so that on presentation of the arm to the mounting structure the arm is guided into a position where it is properly located so as to mate with the mounting structure and for the manually operative latching mechanism to be engaged to retain the arm and the mounting structure together. One or both of the arm and the mounting structure may comprise a resilient element which snaps into positive engagement with the other of the arm and the mounting structure when the two are mated together, in such a way as to resist removal of the arm from with the mounting structure. In addition, one or both of the arm and the mounting structure may comprise a mechanism that is manually operable to restrain the arm in engagement with the mounting structure.

Each mounting structure may be fast with an article of operating theatre furniture, or with another part of the structure of an operating theatre. For example, a mounting structure may be attached to the surface of or embedded within the floor, wall or ceiling of the operating theatre; or a mounting structure may be attached to or embedded within an item of operating theatre furniture such as a trolley, bed, pedestal or table. The mounting structure itself may be moveable, such that it is not permanently fixed to an article of operating theatre furniture, or to part of the structure of an operating theatre, and may be able to be repositioned within the operating theatre.

It is preferred that multiple ones, and preferably all, the mounting structures in an operating theatre are configured similarly, so that any of them can each accommodate and fixedly retain a particular robot arm. Similarly, it is preferred that multiple ones, and preferably all, of the robot arms in an operating theatre are configured similarly, so that any of them can be accommodated and fixedly retained by a particular mounting structure. This allows for the arrangement of the arms to be flexible, so that the most suitable configuration may be chosen for the specific surgical procedure being performed.

The mounting structure may comprise an electrical connection for powering the robot arm. The electrical connection may comprise two or more exposed conductive elements that are configured to contact the arm when the arm is fully engaged with the mounting structure. The mounting structure may comprise a communication connection for conveying data signals to or from the robot arm. The arm may be configured so that motors or other drive mechanisms located within the arm are responsive to electrical control signals received at the interface with the mounting structure to reconfigure the arm. Each robot arm may be electrically and communicatively linked via its respective mounting structure to a control station 13 (see FIG. 1) from where the movement of each arm can be controlled by a surgeon. It is preferred that the arm and the mounting structure are configured so that electrical connections to power the motion of the arm are made by virtue of the arm being mated to the mounting structure. In this way the need for additional cables to be connected and disconnected when the arm is moved from one mounting structure to another can be avoided.

The manually operable latching mechanism may be manipulated by the hand of an operator, who may be a theatre technician or surgical assistant, to connect or disconnect the robot arm from the mounting structure. The manually operable latching mechanism is such that the robot arm does not require fixing to the mounting structure via bolts, brackets or other conventional fastener devices, bonding or mounting methods and does require the use of tools to fix the arms in place. These fixing methods are typically permanent, or semi-permanent, making subsequent removal and reconfiguration of the arms when fixed in such a manner a lengthy procedure that is difficult and inconvenient to perform prior to surgery. A latching mechanism that is manually operable allows the configuration of robot arms to be altered quickly and easily between procedures.

It is useful for the latching mechanism to prevent both rotational and translational motion of the arm once locked in to the mounting structure, to prevent unwanted movements of the arm during a surgical procedure, which may harm the patient.

The manually operable latching mechanism may be integral with the arm, the mounting structure or have components in both the arm and the mounting structure which interconnect.

Figure 3:
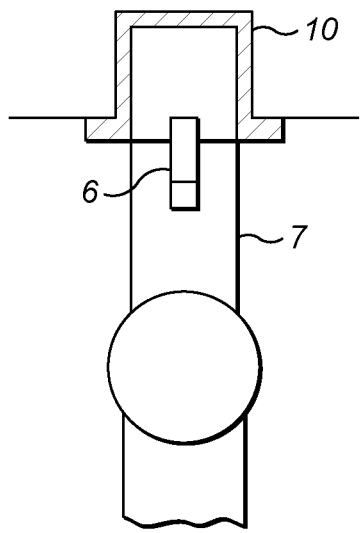
FIG. 3 shows a manually operable latching mechanism for fixing a robot arm to a mounting structure, whereby the robot arm is fixed in place via a latch device on the outside of the interface between the robot arm and the mounting structure.

The manually operable latching mechanism may fix the arm in place in the mounting structure via at least one latch device on the outside of the interface between the robot arm and the mounting structure, as shown in FIG. 3.

Figure 4:
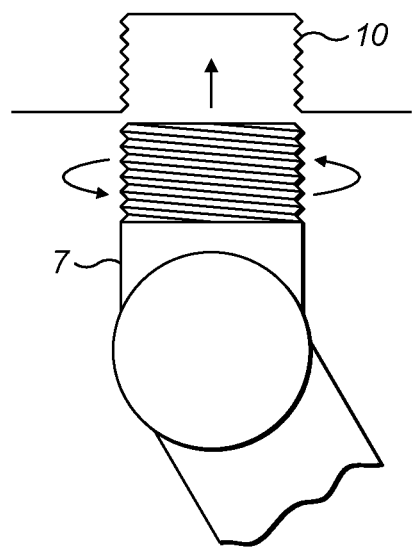
FIG. 4 shows a manually operable latching mechanism where the latching mechanism is integral with the robot and arm and the mounting structure, comprising oppositely threaded parts on the robot arm and mounting structure which connect.

The manually operable latching mechanism may comprise oppositely threaded components integral with each of the arm and mounting structure, as shown in FIG. 4. The arm may be screwed in to mate with the mounting structure, and unscrewed to subsequently remove the arm from the mounting structure.

Figure 5:
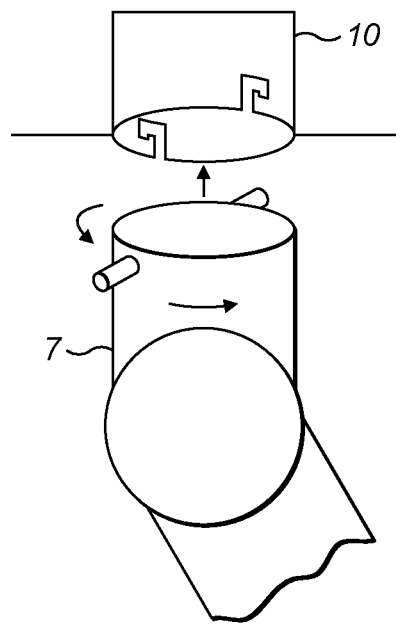
FIG. 5 shows a manually operable latching mechanism where the latching mechanism is integral with the robot and arm and the mounting structure, comprising a bayonet mount.

Alternatively, the manually operable latching mechanism may comprise a bayonet mount consisting of a cylindrical male part with one or more radial pins integral with the robot arm, and a female receptor with matching L-shaped slot(s) and with spring(s) integral with the mounting structure, as shown in FIG. 5. The pin slides into the vertical arm of the L, rotates across the horizontal arm, then is pushed slightly upwards into a short vertical section by the spring, restraining the arm in place in two translational axes. To disconnect, the two parts are pushed together to move the pin out of the short vertical section while twisting in the opposite direction than for connecting, and then pulling apart.

Figure 6:
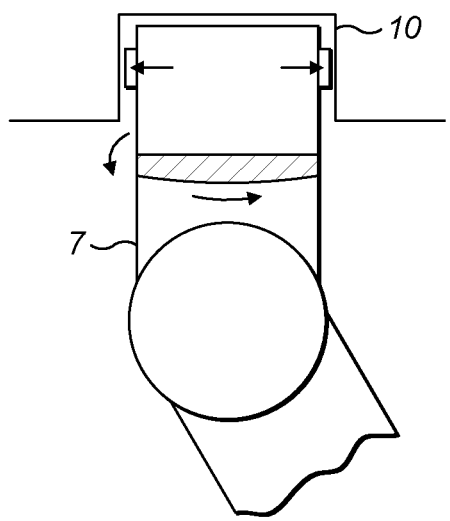
FIG. 6 shows a manually operable latching mechanism comprising pads which may be actuated to extend laterally from the proximal end of the arm to engage with an interior rim of the mounting structure.

In another embodiment, the manually operable latching mechanism may comprise pads which are capable of being actuated to extend laterally from the proximal end of the arm to engage with an interior rim of the mounting structure, as shown in FIG. 6. The pads may be actuated via a rack and pinion mechanism which the technician may operate via a handle on the robot arm.

The manually operable latching mechanism may comprise a visual flag to indicate to the operator that the robot arm is properly latched to the mounting structure. This may help to prevent the robot arm from becoming detached from the mounting structure and falling onto the floor, causing damage to the arm, or landing on the patient or surgical team during the procedure.

Each robot arm, mounting structure and manually operable latching mechanism may have a surface configured for improved grip, which is beneficial if the operator is wearing surgical gloves, or if their hands are covered in a surgical ointment, lotion or disinfectant. For example, surface texture may be added by knurling, by adding ridges, bumps or other surface detail, or by rubberising.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic system comprising:
 a surgical robot arm having at least six degrees of freedom, the arm having a distal end configured to attach to a surgical tool and a proximal end; and
 amounting structure embedded within an item of operating theatre furniture or embedded within the floor, wall or ceiling of an operating theatre and configured to mate to the proximal end of the arm so as to hold the proximal end of the arm spatially fixed, the mounting structure being configured to receive the proximal end of the arm in a direction along a longitudinal axis of the arm and comprising an electrical connection configured to power the robot arm;

wherein the system comprises a manually operable latching mechanism whereby the arm can be attached to and released from the mounting structure.

2. The surgical robotic system of claim 1, wherein the manually operable latching mechanism is integral with the surgical robot arm.

3. The surgical robotic system of claim 1, wherein the manually operable latching mechanism is integral with the mounting structure.

4. The surgical robotic system of claim 1, wherein the mounting structure comprises a socket.

5. The surgical robotic system of claim 1, wherein the mounting structure has side walls that abut the proximal end of the arm when the arm is engaged with the mounting structure.

6. The surgical robotic system of claim 1, wherein the mounting structure comprises a frustoconical socket.

7. The surgical robotic system of claim 1, wherein the mounting structure comprises a communication connection configured to convey data signals to or from the surgical robot arm.

8. A suite of surgical robotic equipment comprising:
a surgical robot arm having at least six degrees of freedom, the arm having a distal end configured to attach to a surgical tool and a proximal end; and
a plurality of mounting structures, each mounting structure being embedded within an item of operating theatre furniture or embedded within the floor, wall or ceiling of an operating theatre and configured to mate to the proximal end of the surgical robot arm so as to hold the proximal end of the arm spatially fixed, each mounting structure being configured to receive the proximal end of the arm in a direction along a longitudinal axis of the arm and comprising an electrical connection configured to power the robot arm;

wherein the suite comprises a manually operable latching mechanism whereby the arm can be attached to and released from any of the plurality of mounting structures.

9. The suite of surgical robotic equipment of claim 8, wherein the manually operable latching mechanism is integral with the robot arm.

10. The suite of surgical robotic equipment of claim 8, wherein the manually operable latching mechanism is integral with the mounting structure.

11. The suite of surgical robotic equipment of claim 8, wherein each of the plurality of mounting structures comprises a socket.

12. The suite of surgical robotic equipment of claim 8, wherein each of the plurality of mounting structures has side walls that abut the proximal end of the arm when the arm is engaged with the mounting structure.

13. The suite of surgical robotic equipment of claim 8, wherein each of the plurality of mounting structures comprises a frustoconical socket.

14. The suite of surgical robotic equipment of claim 8, wherein each of the plurality of mounting structures provides a communication connection configured to convey data signals to or from the surgical robot arm.

15. The suite of surgical robotic equipment of claim 8, comprising at least one further surgical robot arm having at least six degrees of freedom, each further arm having a distal end configured to attach to a surgical tool and a proximal end, the proximal end of the at least one further arm being configured to mate to each of the plurality of mounting structures.

* * * * *